United States Patent [19]

Wehowsky et al.

[11] Patent Number: 4,960,543
[45] Date of Patent: Oct. 2, 1990

[54] URETHANE MADE FROM ALIPHATIC FLUORINATED ALCOHOLS, ISOCYANATES AND SUBSTITUTED AROMATIC COMPOUNDS, A PROCESS FOR THEIR PREPARATION, AND THEIR USE

[75] Inventors: Frank Wehowsky, Burgkirchen; Rolf Kleber, Neu-Isenburg; Lothar Jaeckel, Flörsheim am Main, all of Fed. Rep. of Germany

[73] Assignee: Hoechst Aktiengesellschaft, Frankfurt am Main, Fed. Rep. of Germany

[21] Appl. No.: 289,913

[22] Filed: Dec. 27, 1988

[30] Foreign Application Priority Data

Dec. 29, 1987 [DE] Fed. Rep. of Germany ....... 3744423

[51] Int. Cl.$^5$ ............................................. C09B 11/06
[52] U.S. Cl. .................................................... 560/26
[58] Field of Search ........................ 260/395; 560/133

[56] References Cited

U.S. PATENT DOCUMENTS 4,782,175 11/1988 Wehowsky ........................... 560/26

FOREIGN PATENT DOCUMENTS 0172717 2/1986 European Pat. Off. .
0253186 1/1988 European Pat. Off. .

Primary Examiner—Bruce Gray

[57] ABSTRACT

Urethanes made from aliphatic fluorinated alochols, isocyanates and substituted aromatic compounds, a process for their preparation, and their use.

The novel urethanes are synthesized from an aliphatic fluorinated alcohol, an isocyanate and a specific substituted phenol or aniline compound. They are prepared by reacting an aliphatic fluorinated alcohol with a di- or triisocyanate to form a fluorinated alcohol/isocyanate adduct and reacting this adduct with a certain substituted phenol or aniline to form the urethanes intended. The novel urethanes are preferably used for oleophobic and hydrophobic finishing of textiles and leather.

1 Claim, No Drawings

URETHANE MADE FROM ALIPHATIC FLUORINATED ALCOHOLS, ISOCYANATES AND SUBSTITUTED AROMATIC COMPOUNDS, A PROCESS FOR THEIR PREPARATION, AND THEIR USE

The invention relates to urethanes made from aliphatic fluorinated alcohols, isocyanates and substituted aromatic compounds. The invention furthermore relates to a process for the preparation of these urethanes and to their use.

European Patent Application No. 0,172,717-A2 discloses to improve the textile-finishing properties of urethanes made from at least one aliphatic fluorinated alcohol containing a perfluoroalkyl group as the fluorine component and a tris(isocyanatoalkane)biuret as the isocyanate component by incorporation of a modifying group. The modifying group can be an aromatic, aliphatic or alicyclic compound or a mixture of such compounds having one or more active hydrogen atoms (the compounds are linked to the isocyanate groups via the active hydrogen atoms). Of the modifiers mentioned, essentially only aliphatic compounds are described in greater detail.

Urethanes which contain, in the molecule, at least one perfluoroalkyl group as the aliphatic fluorinated alcohol, an isocyanate and, if appropriate, at least one epichlorohydrin group and at least one aromatic dihydroxy, diamino, aminohydroxy, aminocarboxy or aromatic hydroxycarboxy compound which has been added by means of an active hydrogen atom have also already been proposed for textile finishing, these aromatic compounds being the modifying components (cf. European Patent Application 0,253,186-A2). These urethanes have very good properties with respect to textile finishing.

Further urethanes made from aliphatic flourinated alcohols, isocyanates and aromatic compounds and representing excellent textile-finishing agents have now been found. It has namely been found that specific substituted phenol and aniline derivatives are particularly effective modifying components. The novel urethane compounds are accordingly composed of at least one perfluoroalkyl group (the aliphatic fluorinated alcohol), an isocyanate and, if appropriate, at least one epichlorohydrin group and at least one aliphatic- or aromatic-substituted phenol or aniline compound which has been added by means of an active hydrogen atom.

The urethanes according to the invention conform to the general formula 1 below y denotes a number from 0 to 10, preferably 1 to 5,
m denotes a number from 1 to 2, and
n denotes a number from 1 to 2, where the sum of m+n is at most 3, A denotes one of the groups conforming to the formulae 2 to 10 below (the isocyanate-free radicals):

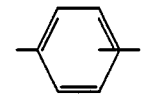 (2)

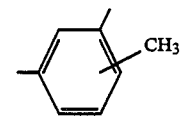 (3)

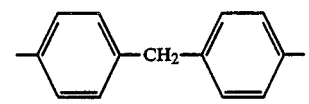 (4)

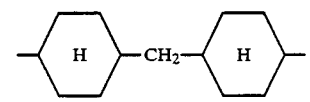 (5)

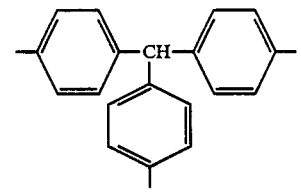 (6)

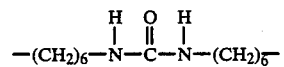 (7)

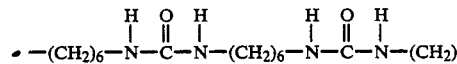 (8)

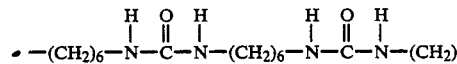 (9)

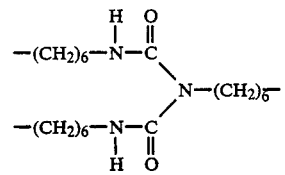 (10)

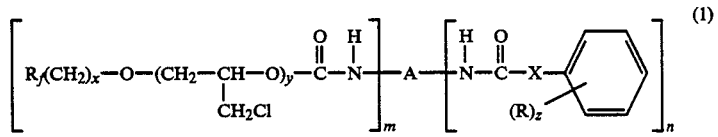 (1)

in which:

$R_f$ denotes a perfluoroalkyl group having 4 to 20 carbon atoms, preferably 6 to 16 carbon atoms, or an $R_f'SO_2NR^1$ group in which $R_f'$ is a perfluoroalkyl group having 4 to 20 carbon atoms, preferably having 6 to 16 carbon atoms, and $R^1$ is H or an alkyl group having 1 to 4 carbon atoms, x denotes an integer from 1 to 4, preferably 2, X denotes —O— or —NH—, z denotes 1, 2 or 3, preferably 1 or 2, and R denotes an alkyl group having 1 to 18 carbon atoms, preferably 1 to 12 carbon atoms, an alkenyl group having 2 to 18 carbon atoms, preferably 2 to 12 carbon atoms, an aryl group or an alkaryl group, it also being possible for R to have several of these meanings.

Of the meanings indicated for $R_f$, the perfluoroalkyl group having 4 to 20 carbon atoms, preferably 6 to 16 carbon atoms, is preferred. The perfluoroalkyl group may be straight-chain or branched; in the case of a branched perfluoroalkyl group, the end-branched perfluoroalkyl group is preferred. Of the two perfluoroalkyl groups, the straight-chain or branched, the straight-chain perfluoroalkyl groups are preferred. The perfluoroalkyl radical is generally a mixture of perfluoroalkyl groups having the abovementioned number of carbon atoms.

A is preferably a toluylene group or one of the three groups conforming to the formulae 8 to 10 (these three groups are generally in the form of a mixture).

In detail, the following applies to the meanings of R: the alkyl and alkenyl groups may be straight-chain or branched, and the alkenyl groups preferably have a maximum of three double bonds. The aryl group may be monosubstituted or polysubstituted, preferably monosubstituted to trisubstituted. Preferred representatives of R as an aryl group are phenyl or phenyl which is monosubstituted to trisubstituted by $C_1$ to $C_6$-alkyl. The alkaryl group preferably comprises an alkyl group which preferably has 1 to 4 carbon atoms and is monosubstituted to trisubstituted by phenyl or phenyl which is monosubstituted to trisubstituted by $C_1$ to $C_6$-alkyl, or by 2 to 3 hydroxyphenyl groups each of which may be monosubstituted to disubstituted by $C_1$ to $C_6$-alkyl (the $C_1$ to $C_4$-alkyl and $C_1$ to $C_6$-alkyl mentioned may be straight-chain or branched).

The preparation of the urethanes according to the invention can be seen from the general formula 1 and is described below in greater detail. They are prepared by reacting an aliphatic fluorinated alcohol of the formula

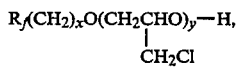

in which $R_f$, x and y are as defined above, with a di- or triisocyanate conforming to one of the groups of the formulae 2 to 10, to form the adduct of the formula

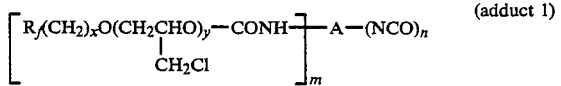 (adduct 1)

in which $R_f$, x, y, m, n and A are as defined above, and reacting this adduct with a substituted phenol or aniline of the formula below

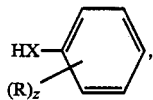

in which X, R and z are as defined above, to form the urethanes according to the invention of the formula 1 given.

The preparation of the compounds according to the invention is described in detail below.

To prepare the adduct 1, aliphatic fluorinated alcohols containing a perfluoroalkyl group are employed in the form of a perfluorohydroalkanol or perfluorosulfonamidoalkanol; if appropriate, they also contain at least one epichlorohydrin group (corresponding to the meaning of y in the formula 1). Perfluorohydroalkanols and perfluorosulfonamidoalkanols as employed for the preparation of the adduct 1 when y is zero in the formula 1 has been known for a long time and therefore need not be described in greater detail. The aliphatic fluorinated alcohols containing a perfluoroalkyl group and containing epichlorohydrin groups are obtained by reacting, for example, perfluoroalkylethanol (as the perfluorohydroalkanol) or, for example, perfluoroalkylsulfonamidoethanol (as the perfluorosulfonamidoalkanol) with epichlorohydrin (boiling point under standard conditions 116° C.), if appropriate in the presence of Lewis acids as catalyst, at a temperature of 30° to 100° C., preferably 40° to 70° C., the ethanol compound and the epichlorohydrin being employed in the molar ratio of about 1:y (y has the meaning in question). With respect to the perfluoroalkyl radical, the perfluorohydroalkanol and the perfluorosulfonamidoalkanol are generally inexpensive, commercially available mixtures essentially having 6 to 20 carbon atoms. The nature of the Lewis acid is not crucial. $BF_3$, boron trifluoride diethyl etherate, $SnCl_4$, $SbCl_5$, $TiCl_4$, $FeCl_3$, $PF_5$ and/or dibutyltin dilaurate are preferred, with boron trifluoride diethyl etherate being particularly preferred. The amount of catalyst is generally 0.01 to 5% by weight, preferably 0.1 to 1% by weight, based on the perfluoroalkylethanol. The reaction is preferably carried out with stirring and at the pressure established. The reaction duration is in the range from about 0.5 to 7 hours. It may be expedient to employ a solvent. Preferred solvents are halogenated hydrocarbons, such as carbon tetrachloride, trichloroethylene, 1,2-dichloroethane, trichloroethane and trifluorotrichloroethane; ketones, such as methyl ethyl ketone and cyclohexanone; and ethers, such as diisopropyl ether and tetrahydrofuran. The reaction in question proceeds quantitatively. The solvent optionally used is distilled off from the reaction product obtained, any volatile components present, such as unreacted epichlorohydrin, also being removed. For reasons for expediency, the distillation can also be carried out in vacuo (water-pump vacuum). The Lewis acid employed as catalyst, which does not interfere with the subsequent reaction with isocyanate, can be washed out or neutralized using alkaline agents, preferably using an aqueous sodium bicarbonate solution or an amine such as triethylamine. The aliphatic fluorinated alcohol containing a perfluoroalkyl group and containing epichlorohydrin groups is a waxy, yellow product.

To prepare the adduct 1, a procedure is preferably followed in which an aliphatic fluorinated alcohol containing a perfluoroalkyl group and, if appropriate, containing at least one epichlorohydrin group (corresponding to the meaning of y in the formula 1) is reacted with an isocyanate conforming to the formulae 2 to 10, at a temperature of from 70° to 150° C., preferably 90° to 130° C., the aliphatic fluorinated alcohol and the isocyanate being employed in the molar ratio which arises from the intended meaning for m and n in the formula for the adduct 1. The reaction is preferably carried out with stirring and at the pressure established and—if expedient, for example to shorten the reaction time—in the presence of the abovementioned Lewis acid catalysts. It is also possible to employ solvents, for example esters. The reaction duration is in the range 1 to 15 hours. The isocyanate is frequently a commercially available isocyanate mixture. Thus, the toluylene diisocyanate generally comprises about 80% by weight of 2,4-toluylene diisocyanate and 20% by weight of 2,6-toluylene diisocyanate. The isocyanates conforming to the groups of formulae 8 to 10 are also generally in the form of mixtures. A commercially available and preferred mixture of this type comprises the three isocyanates in question, the isocyanate conforming to the formula 10 being present in an amount of at least 50% by weight, based on the mixture (the isocyanate of the formula 10 is thus the principal component in this mixture). The reaction of the aliphatic fluorinated alcohol in question with isocyanate to form the adduct 1 proceeds quantitatively. The products obtained can be purified if necessary, for example volatile components can be removed by distillation. The adduct 1 is a waxy, yellow product.

To prepare the urethanes of the formula 1 according to the invention, a procedure is preferably followed in which the adduct 1 is reacted with a phenol or aniline compound of the stated formula at a temperature of from 70° to 150° C., preferably 90° to 130° C., the adduct 1 compound and the phenol or aniline compound being employed in a molar ratio such that the molar amount of phenol or aniline compound corresponds to the free isocyanate groups present in the adduct 1 employed. The reaction is preferably carried out with stirring and at the pressure established and—if expedient, for example to shorten the reaction time—in the presence of the abovementioned Lewis acid catalysts. It is also possible to employ solvents, for example esters. The reaction duration is in the range 1 to 40 hours. The reaction of the adduct 1 with the phenol or aniline compound to form the urethanes of the formula 1 according to the invention proceeds quantitatively. The urethane obtained can be purified if necessary, for example volatile components can be removed by distillation. The urethanes according to the invention are waxy, yellow to brown products.

The urethanes according to the invention are surprisingly good textile-treatment agents. They impart, in particular, excellent hydrophobicity and oleophobicity on the textiles. Furthermore, they have, to a large extent, the property of standing up to the aggressive conditions to which the finished textiles are subjected, for example during stretching, texturing and, in particular, during dyeing and washing, without any loss of action. An unexpected and particularly great advantage of the compounds according to the invention is that they can also be employed in customary textile-treatment preparations, for example in spinning preparations, where they do not lose their excellent action.

The textile material may be of natural and/or synthetic nature. It preferably comprises nylon, polyester and/or polyacrylonitrile, nylon being particularly preferred. The textile material can be in any desired form, thus, for example, as filaments, fibers, yarn, flocks, woven fabric, knitted fabric, carpet or non-woven fabric. The amount of compound according to the invention applied is selected so that 0.02 to 1% by weight of fluorine, preferably 0.04 to 0.4% by weight of fluorine, is present on the textile material, calculated from the amount of fluorine in the compound according to the invention; percent by weight based on the textile material treated. Treatment of the textile material with the urethanes according to the invention is generally carried out either via the abovementioned textile-treatment preparations into which the urethanes according to the invention have been incorporated, or using solutions, emulsions or dispersions prepared just from the urethanes. They are generally present in the solutions, emulsions or dispersions or in the textile-treatment preparations in a concentration of from 5 to 40 or 0.5 to 5% by weight respectively, preferably 8 to 30 or 1 to 3% by weight respectively.

The textiles are treated with the solutions, emulsions or dispersions mentioned by customary methods, thus, for example, by spraying, dipping, pad-mangling or the like. The impregnated textile material is subsequently dried and subjected to heat treatment. The heat treatment is generally carried out by heating the textile material to a temperature of from 130° to 200° C. and keeping it at this temperature for 10 seconds to 10 minutes. The textile material finished with the urethanes according to the invention has the abovementioned excellent properties. The compounds according to the invention are also highly suitable for hydrophobic and oleophobic finishing of leather. Examples of leather which may be mentioned are cowhide leather, goatskin leather, sheepskin and pigskin leather. The amount of compounds according to the invention applied is selected so that 0.05 to 1.5% by weight of fluorine, preferably 0.1 to 1% by weight of fluorine, is present on the leather, calculated from the amount of fluorine in the compound; percent by weight based on the treated leather. The customary procedures for leather finishing can be employed for application.

The invention is now described in greater detail with reference to examples.

Compounds according to the invention

EXAMPLE 1

8 kg (15.7 mol) of commercially available perfluoroalkylethanol mixture with perfluoroalkyl $=C_8F_{17}$-$C_{16}F_{33}$ (OH number=106), 8 kg of 1,2,2-trifluorotrichloroethane (CFCl$_2$ —CF$_2$Cl; bp=48° C.) as solvent and 50 g of boron trifluoride diethyl etherate as catalyst (that is 0.6% by weight of catalyst, based on perfluoroalkylethanol) were introduced into a glass flask equipped with a stirrer, reflux condenser, thermometer, dropping funnel and heating bath. 2.9 kg (31.4 mol) of epichlorohydrin were added dropwise to this solution at 45° C., after which the mixture was kept at the boiling point of the solvent for 3 hours. The solvent employed was subsequently removed by distillation in vacuo (water-pump vacuum), to give a waxy, yellow product. The perfluoroalkyl ethanol: epi-chlorohydrin molar ratio in the aliphatic fluorinated alcohol thus obtained is 1:2 (in formula 1, y has the value 2, given by taking the mean of 1 to 8 adducted epichloro-hydrin units).

The reaction of the aliphatic fluorinated alcohol with isocyanate to form the fluorinated alcohol/isocyanate adduct (adduct 1) was carried out in a glass flask equipped with stirrer, reflux condenser with drying tube, thermometer and heating bath.

85.0 g (0.13 mol) of the aliphatic fluorinated alcohol and 35.7 g (0.065 mol) of triisocyanate conforming to the formula 10, more precisely a commercially available mixture of the three isocyanates conforming to the formulae 8, 9 and 10 with the triisocyanate as the principal component, were introduced into the flask (that is a molar ratio of 2:1), and the mixture was kept at 110° C. for 4 hours with stirring. 5 drops of dibutyltin dilaurate were then added to the mixture, after which it was kept at 110° C. for 3 hours with stirring in order to react further. The fluorinated alcohol/isocyanate adduct (adduct 1) obtained was a waxy, yellow product.

The reaction of the adduct 1 with the substituted phenols or anilines to be employed according to the invention was likewise carried out in a glass flask equipped with stirrer, reflux condenser with drying tube, thermometer and heating bath.

100.0 g (62.6 mmol) of adduct 1 and 15.1 g (62.8 mmol) of para-hydroxystyrene were introduced into the flask (that is a molar ratio of 1:1), and the mixture was kept at 110° C. for 35 hours with stirring. 112 g, that is 97% by weight of theory, of the compound according to the invention were obtained in the form of a waxy, brown product. The empirical composition of the compound according to the invention containing an aliphatic fluorinated alcohol, an isocyanate and para-hydroxystyrene in the molecule (molar ratio 2:1:1) conforms to the formula B1 given in the table after the examples.

EXAMPLE 2

231.4 g (0.12 mol) of adduct 1 from example 1 and 47.5 g (0.12 mol) of styrylphenol (that is a molar ratio of 1:1) were introduced into the abovementioned glass flask, and the mixture was kept at 110° C. for 12 hours with stirring. 5 drops of dibutyltin dilaurate were then added to the mixture, after which it was kept at 110° C. for 4 hours with stirring in order to react further. 277.8 g, that is 99.6% by weight of theory, of the compound according to the invention were obtained in the form of a waxy, brown product. The empirical composition of the compound according to the invention containing an aliphatic fluorinated alcohol, an isocyanate and styrylphenol in the molecule (molar ratio 2:1:1) conforms to the formula B2 given in the table mentioned.

EXAMPLE 3

To prepare a further adduct 1, 162.0 g (0.32 mol) of the perfluoroalkyl ethanol of example 1, 216.0 g (0.32 mol) of the aliphatic fluorinated alcohol of example 1 and 181.3 g (0.32 mol) of the triisocyanate of example 1 (that is a molar ratio of 1:1:1) were introduced into the glass flask indicated in example 1, and the mixture was kept at 110° C. for 3 hours with stirring; after addition of 9 drops of dibutyltin dilaurate to the mixture, the latter was stirred at 110° C. for a further 3 hours. The fluorinated alcohol/isocyanate adduct (adduct 1) obtained was a waxy, yellow product.

To carry out the reaction according to the invention of this adduct 1, 559.0 g (0.32 mol) of the adduct and 83.8 g (0.32 mol) of para-dodecylphenol (that is a molar ratio of 1:1) were introduced analagously to example 1 into the flask, and the mixture was kept at 110° C. for 5 hours with stirring. 638 g, that is 99% by weight of theory, of the compound according to the invention were obtained in the form of a waxy, brown product. The empirical composition of the compound according to the invention containing an aliphatic fluorinated alcohol, an isocyanate and paradodecyl phenol in the molecule (molar ratio 2:1:1) conforms to the formula B3.

EXAMPLE 4

Batch:
289.3 g (0.15 mol) of adduct 1 of example 3.
22.5 g (0.15 mol) of para-tert.-butylphenol.
Procedure as in example 3.

Yield: 304 g, that is 97.5% by weight of theory, of the compound according to the invention in the form of a waxy, brown product. The empirical composition of the compound according to the invention containing an aliphatic fluorinated alcohol, an isocyanate and para-tert.-butylphenol in the molecule (molar ratio 2:1:1) conforms to the formula B4.

EXAMPLE 5

Batch:
289.3 g (0.15 mol) of adduct 1 of example 3.
46.1 g (0.15 mol) of tris(para-hydroxyphenylethane).
Procedure as in example 3.

Yield: 330 g, that is 98.5% by weight of theory, of the compound according to the invention in the form of a waxy, brown product. The empirical composition of the compound according to the invention containing an aliphatic fluorinated alcohol, an isocyanate and tris(-para-hydroxyphenylethane) in the molecule (molar ratio 2:1:1) conforms to the formula B5.

TABLE

| No. | Chemical formulae of the compounds according to the invention of Examples 1 to 5 |
| --- | --- |
| B1 | $\left[ (C_8F_{17}-C_{16}F_{33})-CH_2CH_2O-(CH_2CHO)_2-CONH \atop \quad\quad\quad\quad\quad\quad\quad\quad\quad\quad\quad CH_2Cl \right]_2 -A-NHCO-O-\bigcirc-CH=CH_2$ |
| B2 | $\left[ (C_8F_{17}-C_{16}F_{33})-CH_2CH_2O-(CH_2CHO)_2-CONH \atop \quad\quad\quad\quad\quad\quad\quad\quad\quad\quad\quad CH_2Cl \right]_2 -A-NHCO-O-\bigcirc\underset{CH_3}{\overset{}{\underset{|}{CH}}}-\bigcirc$ |
| B3 | $(C_8F_{17}-C_{16}F_{33})-CH_2CH_2O-CONH$<br>$(C_8F_{17}-C_{16}F_{33})-CH_2CH_2O-(CH_2CHO)_2-CONH$<br>$\quad\quad\quad\quad\quad\quad\quad\quad\quad\quad\quad\quad CH_2Cl$<br>$\rangle A-NHCO-O-\bigcirc-C_{12}H_{25}$ |

| No. | Chemical formulae of the compounds according to the invention of Examples 1 to 5 |
|---|---|

TABLE-continued

B4

$(C_8F_{17}-C_{16}F_{33})-CH_2CH_2O-CONH$
$(C_8F_{17}-C_{16}F_{33})-CH_2CH_2O-(CH_2CHO)_2-CONH$
$\phantom{xxxxxxxxxxxxxxxxxxxxxxxx}|$
$\phantom{xxxxxxxxxxxxxxxxxxxxxxxx}CH_2Cl$

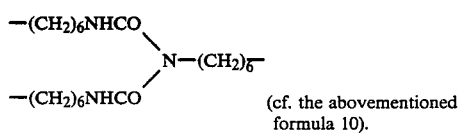

B5

$(C_8F_{17}-C_{16}F_{33})-CH_2CH_2O-CONH$
$(C_8F_{17}-C_{16}F_{33})-CH_2CH_2O-(CH_2CHO)_2-CONH$
$\phantom{xxxxxxxxxxxxxxxxxxxxxxxx}|$
$\phantom{xxxxxxxxxxxxxxxxxxxxxxxx}CH_2Cl\ \cdot$ In the formulae B1 to B5, A represents $-(CH_2)_6NHCO$
$\phantom{xxxxxxxx}\diagdown$
$\phantom{xxxxxxxxxx}N-(CH_2)_6-$
$\phantom{xxxxxxxx}\diagup$
$-(CH_2)_6NHCO$ (cf. the abovementioned formula 10).

Use of the compounds according to the invention

EXAMPLES I to V

In examples I to V, the compounds B1 to B5 according to the invention were tested using a customary spinning preparation for nylon fibers, in each case containing about 150 g of the compound according to the invention per 1000 g of spinning preparation (the spinning preparation thus comprised water as the principal component, the customary ethoxylated fatty alcohols and long-chain aminoxides as the preparation agent and about 15% by weight of the compound according to the invention). Identical nylon-6 α filaments were in each case treated with each of the five spinning preparations in order to apply sufficient of the compound according to the invention and of the preparation agent onto the filaments so that 0.08% by weight of fluorine and 1% by weight of preparation agent were present on the filaments, percent by weight in each case based on the weight of the filaments. In addition, the filaments were drawn in a customary manner through the spinning preparation, dried and kept at a temperature of 200° C. for 30 seconds (heat treatment, condensation). A woven fabric was in each case produced from the filaments treated in this way. Five woven fabrics containing the compounds B1 to B5 according to the invention were present, a fluorine coating of 0.08% by weight and a preparation agent coating of 1% by weight being present on each woven fabric, percent by weight in each case based on the weight of the fabric.

The oil repellency (oleophobicity) was tested on the five fabrics in accordance with the AATCC testing standard 118—1966, and the water repellency (hydrophobicity) was tested in accordance with DIN 53 888—1965; this was done after the condensation described and after treatment of the condensed fabric for three hours with a boiling alkaline wash. During this treatment, the individual fabrics were boiled in a customary manner for 3 hours in an alkaline washing liquid and subsequently dried; the washing liquid comprised 1 l of water, 1 g of trisodium phosphate and 2 g of a fatty acid polyglycol ester which had been obtained by oxyethylation of 1,4-butanediol using 15 mol of ethylene oxide and subsequent esterification of the oxyethylate using 1 mol of oleic acid.

The results from examples I to V are summarized below:

| Examples and compounds tested | Oil repellency | | Water repellency | |
|---|---|---|---|---|
| | after condensation | after boiling wash | after condensation | after boiling wash |
| I /B1 | 6 | 4 | 5 | 4 |
| II /B2 | 6 | 5 | 5 | 4 |
| III/B3 | 6 | 5 | 5 | 4 |
| IV /B4 | 6 | 5 | 5 | 4 |
| V /B5 | 5 | 4 | 4 | 4 |

The AATCC Test 118—1966 (American Association of Textile Chemists and Colorists) and DIN 53 888—1965 (Deutsche Industrie-Norm) are described below:

In order to determine the oil repellency value in accordance with the AATCC test 118—1966, three drops of a certain test liquid (see below) are, as is known, carefully placed on the textile material to be tested.

Action time: 30 seconds. The value is given at which no apparent wetting of the fabric under the drops (after completion of the action time) has been caused:

| Test liquid | Oil repellency value |
|---|---|
| Paraffin oil | 1 |
| Paraffin oil: n-hexadecane = 65:35 | 2 |
| n-hexadecane | 3 |
| n-tetradecane | 4 |
| n-dodecane | 5 |
| n-decane | 6 |
| n-octane | 7 |
| n-heptane | 8 |

An oil repellency value of 1 denotes the worst repellent effect and an oil repellency value of 8 denotes the best.

In order to determine the water repellency value in accordance with DIN 53 888—1965, the textiles to be tested are, as is known, showered under standardized conditions, the underside of the textile sample simultaneously being rubbed mechanically. The water repellent effect is assessed visually using scores 1 to 5, score 1 denoting the worst repellent effect and score 5 denoting the best.

The test results show that very high oil and water repellency is achieved by means of the urethanes according to the invention, and that the urethanes according to the invention can also be added to textile-treatment preparations.

We claim:

1. A urethane made from an aliphatic fluorinated alcohol an isocyanate and a substituted aromatic compound of the formula

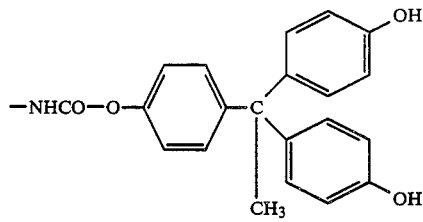

wherein A is 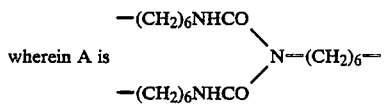

* * * * *